(12) United States Patent
Thompson (10) Patent No.: US 8,374,680 B2
(45) Date of Patent: Feb. 12, 2013

(54) NEEDLELESS CATHETERS AND METHODS FOR TRUE LUMEN RE-ENTRY IN TREATMENT OF CHRONIC TOTAL OCCLUSIONS AND OTHER DISORDERS

(75) Inventor: Dustin Thompson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1171 days.

(21) Appl. No.: 12/106,689

(22) Filed: Apr. 21, 2008

(65) Prior Publication Data

US 2009/0264826 A1  Oct. 22, 2009

(51) Int. Cl.
*A61B 5/05* (2006.01)
(52) U.S. Cl. ........................................ 600/424; 604/528
(58) Field of Classification Search .......... 600/407–424, 600/437–465; 606/130, 41, 42, 159, 167; 604/22, 528–530
See application file for complete search history.

(56) References Cited

U.S. PATENT DOCUMENTS

| | | | |
|---|---|---|---|
| 5,830,222 A | 11/1998 | Makower | |
| 6,068,638 A | 5/2000 | Makower | |
| 6,159,225 A | 12/2000 | Makower | |
| 6,190,353 B1 | 2/2001 | Makower et al. | |
| 6,283,951 B1 * | 9/2001 | Flaherty et al. | 604/529 |
| 6,375,615 B1 | 4/2002 | Flaherty et al. | |
| 6,508,824 B1 | 1/2003 | Flaherty et al. | |
| 6,544,230 B1 * | 4/2003 | Flaherty et al. | 604/164.12 |
| 6,579,311 B1 | 6/2003 | Makower | |
| 6,602,241 B2 | 8/2003 | Makower et al. | |
| 6,655,386 B1 | 12/2003 | Makower et al. | |
| 6,660,024 B1 * | 12/2003 | Flaherty et al. | 600/439 |
| 6,685,648 B2 * | 2/2004 | Flaherty et al. | 600/464 |
| 6,709,444 B1 | 3/2004 | Makower | |
| 6,726,677 B1 * | 4/2004 | Flaherty et al. | 604/528 |
| 6,746,464 B1 * | 6/2004 | Makower | 606/185 |
| 7,729,738 B2 * | 6/2010 | Flaherty et al. | 600/407 |
| 7,849,860 B2 * | 12/2010 | Makower et al. | 128/898 |
| 7,966,057 B2 * | 6/2011 | Macaulay et al. | 600/424 |
| 8,214,015 B2 * | 7/2012 | Macaulay et al. | 600/424 |
| 2004/0147837 A1 * | 7/2004 | Macaulay et al. | 600/424 |
| 2004/0158143 A1 * | 8/2004 | Flaherty et al. | 600/407 |
| 2006/0184011 A1 * | 8/2006 | Macaulay et al. | 600/423 |
| 2006/0241342 A1 * | 10/2006 | Macaulay et al. | 600/104 |
| 2007/0239010 A1 * | 10/2007 | Johnson | 600/439 |
| 2009/0248142 A1 * | 10/2009 | Perkins et al. | 623/1.24 |

* cited by examiner

*Primary Examiner* — Sanjay Cattungal (57) ABSTRACT

A catheter system comprising a) an elongate flexible catheter; b) a lumen that extends from a proximal insertion port to a side outlet opening; c) a penetrating guidewire insertable into the proximal insertion port and thereafter advanceable through the lumen and out of the side outlet opening; and d) an orientation element useable to provide an indication of the trajectory on which the penetrating guidewire will advance from the catheter body. Also disclosed are methods for using such catheter to direct the penetrating guidewire out of the side opening and into the true lumen of a blood vessel when bypassing an obstruction in the blood vessel such as a chronic total occlusion (CTO) of an artery.

10 Claims, 6 Drawing Sheets

NEEDLELESS CATHETERS AND METHODS FOR TRUE LUMEN RE-ENTRY IN TREATMENT OF CHRONIC TOTAL OCCLUSIONS AND OTHER DISORDERS

FIELD OF THE INVENTION

The present invention relates generally to methods and apparatus for medical treatment and more particularly to catheter devices and related methods for bypassing chronic total occlusions of arteries and other procedures.

BACKGROUND

Total or near-total occlusions in arteries can prevent all or nearly all of the blood flow through the affected arteries. Chronic total occlusions (CTOs) can occur in coronary as well as peripheral arteries. It has been estimated that approximately 10% of all angioplasty procedures are currently undertaken for CTOs.

In the past, a number of devices have been developed and/or used for the percutaneous interventional treatment of CTOs, such as special guidewires, low-profile balloons, laser emitting wires, atherectomy devices, drills, drug eluting stents, re-entry catheter, etc. The factor that is most determinative of whether the interventionalist can successfully recannalize a CTO is the interventionalist's ability (or inability) to advance a suitable guidewire from a position within the true lumen of the artery proximal to the CTO, across the CTO lesion (i.e., either through the lesion or around it), and then into the true lumen of the artery at a location distal to the lesion.

In some instances, such as where the occlusive matter is soft or where the occlusion is less than total, the guidewire can simply be pushed through the occlusive matter itself, thereby allowing the guidewire to remain within the artery lumen. However, in other cases, such as where the artery is totally occluded by hard, calcified atherosclerotic plaque, the guidewire may tend to deviate to one side and penetrate through the intima of the artery, thereby creating a neo-lumen called a "subintimal space" (e.g., a penetration tract formed within the wall of the artery between the intima and adventitia). In these cases, the distal end of the guidewire may be advanced to a position distal to the lesion but remains entrapped within the subintimal space. In such instances, it is then necessary to divert or steer the guidewire from the subintimal space back into the true lumen of the artery at a location distal to the CTO lesion.

Copending U.S. patent application Ser. No. 11/613,764 entitled Low Profile Catheters and Methods for Treatment of Chronic Total Occlusions and Other Disorders describes a low-profile catheter device that may be useable to facilitate passage of a guidewire from the subintimal space into the true lumen of the blood vessel and related methods for bypassing CTOs.

A number of other catheters known in the prior art may also be useable to redirect subintimally entrapped guidewires back into the true lumen of the artery. Included among these are the devices described in U.S. Pat. Nos. 5,830,222 (Makower), 6,068,638 (Makower), 6,159,225 (Makower), 6,190,353 (Makower, et al.), 6,283,951 (Flaherty, et al.), 6,375,615 (Flaherty, et al.), 6,508,824 (Flaherty, et al.), 6,544,230 (Flaherty, et al.), 6,655,386 (Makower et al.), 6,579,311 (Makower), 6,602,241 (Makower, et al.), 6,655,386 (Makower, et al.), 6,660,024 (Flaherty, et al.), 6,685,648 (Flaherty, et al.), 6,709,444 (Makower), 6,726,677 (Flaherty, et al.) and 6,746,464 (Makower). One such catheter is currently available as the Pioneer™ catheter from Medtronic Vascular, Inc., Santa Rosa, Calif.

There remains a need in the art for the development of new small diameter catheters that have laterally deployable members (e.g., cannulae, needles, probes, wires, etc.) which may be used to re-enter the true lumen of a blood vessel when bypassing a CTO for other purposes such as delivery of substances, articles or devices to specific target locations within the body.

SUMMARY OF THE INVENTION

In accordance with the present invention there is provided a catheter system comprising; a) an elongate flexible catheter; b) a lumen that extends from a proximal insertion port to a side outlet opening and c) a penetrating guidewire insertable into the proximal insertion port and thereafter advanceable through the lumen and out of the side outlet opening. Optionally, the catheter system may further comprise an orientation element useable to provide an indication of the trajectory on which the penetrating guidewire will advance from the catheter. Also optionally, the catheter may include a tracking guidewire lumen (over-the-wire or rapid exchange) to facilitate advancing the catheter over a previously inserted tracking guidewire. Because the catheters of the present invention may be of relatively small diameter, some embodiments of such catheters may be used by this method for treatment of coronary CTOs as well as CTO in larger peripheral arteries.

Further in accordance with the invention, there is provided a method for bypassing an obstruction in a blood vessel (e.g., a chronic total occlusion or other full or partial obstruction) using the above-summarized catheter system. In this method, a tracking guidewire may be initially advanced into the blood vessel such that the distal end of the guidewire becomes positioned within a subintimal space that extends past the obstruction. Thereafter, the catheter may be advanced over the tracking guidewire and into the subintimal space such that the side outlet opening of the catheter is located distal to the obstruction. If the catheter is equipped with the optional orientation element, such orientation element may be used to adjust the rotational orientation as necessary to ensure or at least increase the likelihood that subsequent advancement of the penetrating guidewire out of the side outlet opening will cause the penetrating guidewire to enter the true lumen of the blood vessel downstream of (i.e., distal to) the obstruction. The penetrating guidewire is then advanced out of the side outlet opening and into the true lumen of the blood vessel downstream of (i.e., distal to) the obstruction. The catheter may then be removed, leaving the penetrating guidewire in place. One or more working device(s) may then be advanced over the penetrating guidewire to create a suitable blood flow channel around the obstruction.

Further aspects, details and embodiments of the present invention will be understood by those of skill in the art upon reading the following detailed description of the invention and the accompanying drawings.

DETAILED DESCRIPTION

The following detailed description, the accompanying drawings are intended to describe some, but not necessarily all, examples or embodiments of the invention. The contents of this detailed description and accompanying drawings do not limit the scope of the invention in any way.

Figure 1:
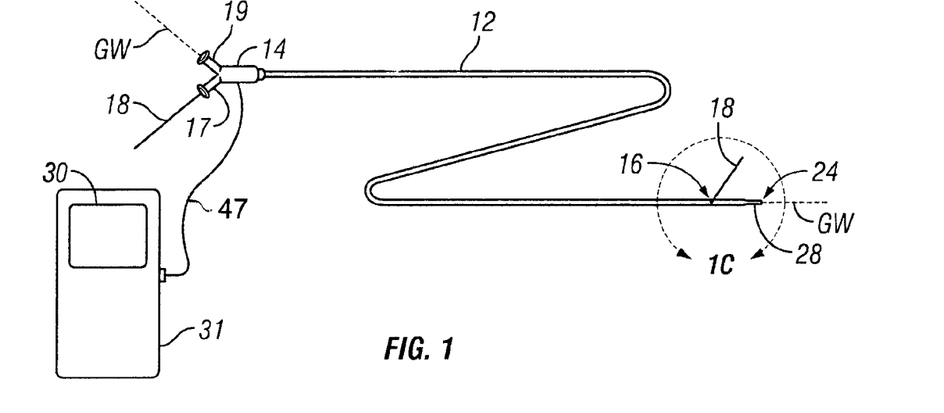
FIG. 1 is a side view of one embodiment of a catheter system of the present invention.

FIG. 1 generally shows one embodiment of a tissue penetrating catheter system 10 if the present invention. This system 10 comprises a flexible catheter 12 having a proximal hub 14 with female Luer ports 17, 19, a side outlet opening 16 and a distal end opening 24. A penetrating guidewire 18 (e.g., a 0.014 in. diameter trocar or stiff guidewire available as (e.g. PERSUADER® 9 guidewire, from Medtronic Vascular, Inc., Santa Rosa, Calif. or ASAHI CONFIANZA®, Abbott Vascular, Redwood City, Calif.) is insertable through port 17 on the proximal Y hub 14 and is advanceable through the catheter 12 and out of side outlet opening 16. Optionally, a tracking guidewire GW (e.g., a 0.014 in. diameter guidewire available as the COUGAR® guidewire from Medtronic Vascular, Inc., Santa Rosa, Calif.) is insertable into port 19 on proximal Y hub 14 and is advanceable through the catheter 12 and out of distal end opening 24. As an alternative to the "over-the-wire" design shown in the drawings, a "rapid exchange" version of the catheter 12 may also be used. In such rapid exchange version of the catheter, the port 19 on proximal Y hub 14 would be replaced by a tracking guidewire insertion port located on the side of the catheter 12 a spaced distance (e.g., 15-30 cm) from its distal end. Optionally, the catheter 12 may incorporate an orientation indicating element 28 which provides, on a monitor screen 30 an indication of the trajectory on which the penetrating guidewire 18 will advance from the catheter body 12 relative to the location of the intended target to which it is desired to advance the penetrating guidewire 18. As explained in more detail below, this orientation indicating element 28 may comprise an imageable marker that may be imaged by an imaging apparatus located either on/in the catheter 12 or elsewhere (e.g., a fluoroscope or other extracorporeal imaging device). In some other embodiments, this orientation indicating element 28 may comprise an on-board imaging apparatus located on or in the catheter 12 that is useable to image the target location to which it is desired to advance the penetrating guidewire 18 (e.g., the true lumen of an artery) along with an electronic or physical indicator of the direction in which, or the trajectory on which, the penetrating guidewire 18 will subsequently advance out of side outlet opening 16. Thus, this optional orientation indicating element 28 provides information which the operator may use to make any necessary adjustments in the position and rotational orientation of the catheter body 12 in situ ensure (or at least increases the probability) that the penetrating guidewire 18 will subsequently advance to the intended target location and not some other location. One specific example of this orientation element 28 is shown in FIGS. 1C through 2B and described in detail below. Other examples of the various types of orientation elements 28 that may be used include but are not limited to those described in U.S. Pat. Nos. 5,830,222 (Makower), 6,068,638 (Makower), 6,159,225 (Makower), 6,190,353 (Makower, et al.), 6,283,951 (Flaherty, et al.), 6,375,615 (Flaherty, et al.), 6,508,824 (Flaherty, et al.), 6,544,230 (Flaherty, et al.), 6,655,386 (Makower et al.), 6,579,311 (Makower), 6,602,241 (Makower, et al.), 6,655,386 (Makower, et al.), 6,660,024 (Flaherty, et al.), 6,685,648 (Flaherty, et al.), 6,709,444 (Makower), 6,726,677 (Flaherty, et al.) and 6,746,464 (Makower) as well as United States Patent Application Publication 2006/0241342 (Macaulay et al.) entitled Optically Guided Penetration Catheters and Their Methods of Use, the entire disclosure of each such patent and published patent applications being expressly incorporated herein by reference.

Figure 1A:
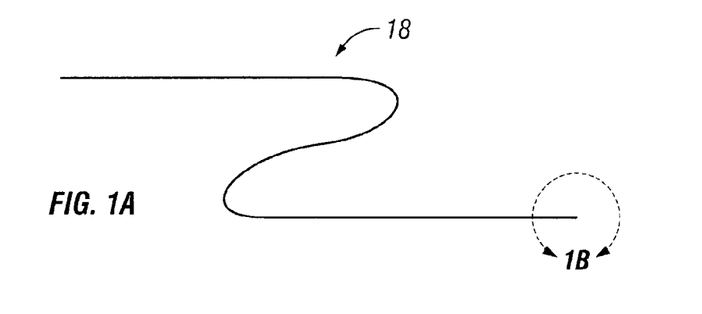
FIG. 1A is a side view of a penetrating guidewire which is one component of the catheter system of FIG. 1.
Figure 1B:
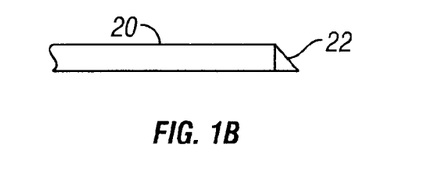
FIG. 1B is an enlarged view of the distal end of the penetrating guidewire of FIG. 1A.
Figures 1C, 1D, 1E, 1F, 2A, 2B:
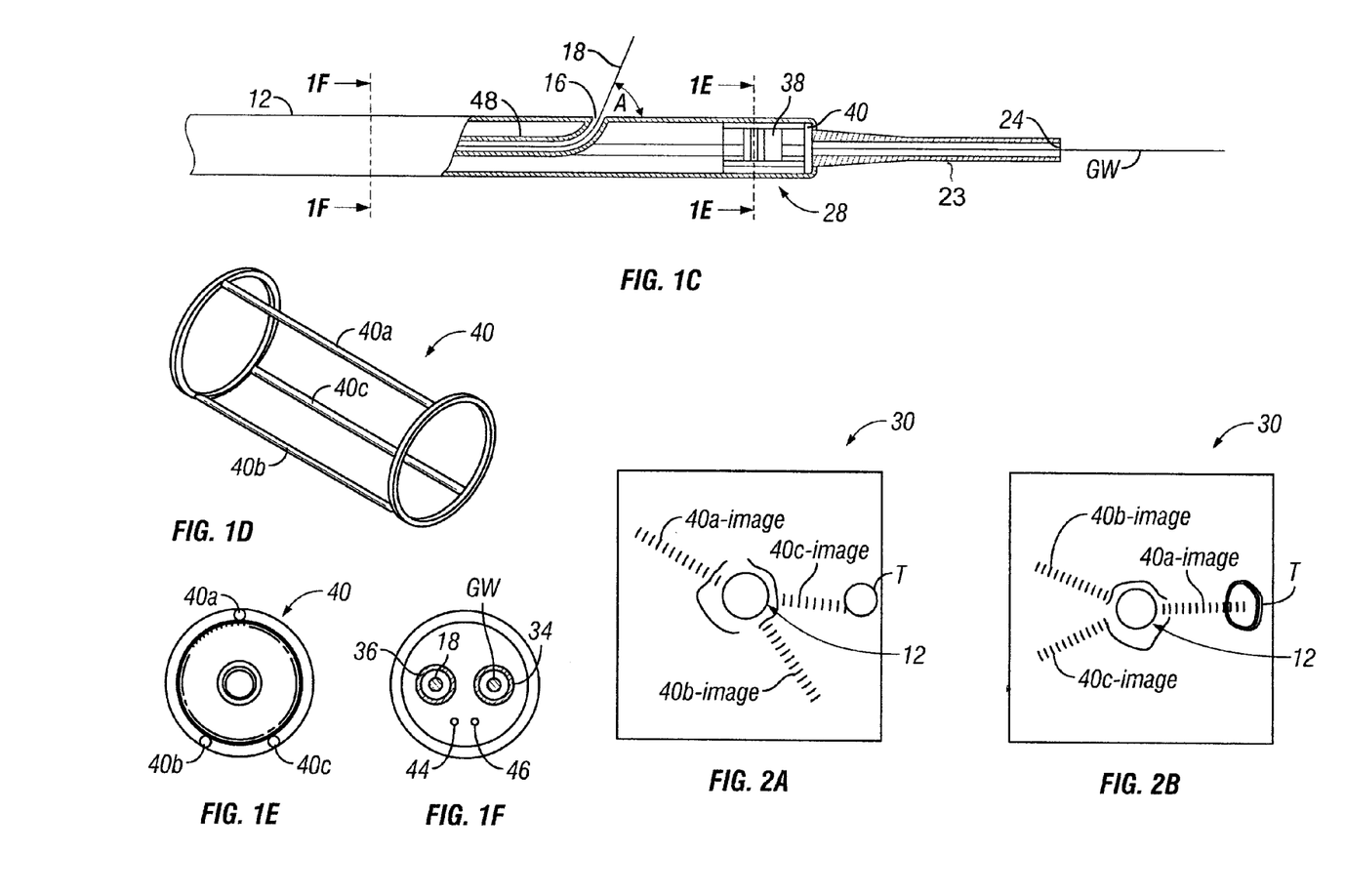
FIG. 1C is an enlarged, partially cut-away side view of a distal portion of the catheter system of FIG. 1.
FIG. 1D is an enlarged view of a marker structure of the catheter system of FIG. 1.
FIG. 1E is a cross-sectional view through line 1E-1E of FIG. 1C.
FIG. 1F is a cross-sectional view through line 1F-1F of FIG. 1C.
FIG. 2A is a schematic diagram of a monitor display indicating that the catheter of FIG. 1 is in an incorrect rotational orientation relative to the target.
FIG. 2B is a schematic diagram of a monitor display indicating that the catheter of FIG. 1 is in a correct rotational orientation relative to the target.

In the example shown in FIGS. 1A and 1B, the penetrating guidewire 18 comprises a flexible guidewire body 20 with a sharp and/or stiff distal tip member 22 located at its distal end. As indicated in FIG. 1C, in some embodiments, the penetrating guidewire 18 may advance out of the side outlet opening 16 on a trajectory that forms an angle A of less than 90 degrees relative to the longitudinal axis of the catheter 12. In the particular example shown, this angle A is approximately 65 degrees.

Also, in this example, the catheter 12 includes an optional tapered distal tip section 23 formed of material that is softer and more flexible than the adjacent distal portion of the catheter 12.

As may be appreciated from FIGS. 1, 1C and 1F, in this example the catheter 12 has a tracking guidewire lumen 34 and a penetrating guidewire lumen 36. A curved, substantially rigid tubular member 48 is located at the distal end of the penetrating guidewire lumen 36 and serves as a guide surface which deflects the penetrating guidewire 18 out of the side outlet opening 16. Also, in the particular embodiment shown, the orientation element 28 comprises an on-board imaging transducer 38 that is positioned within a marker structure 40 near the distal end of the catheter 12. Any suitable type of imaging transducer may be used, including ultrasound, fiber optic (e.g., angioscopic), optical (e.g., optical coherence tomography, etc. This particular imaging transducer 38 comprises a phased array intravascular ultrasound (IVUS) transducer that is operative to image 360º around the catheter 12. This imaging transducer 38 also comprises an annular array of individual crystals or elements coupled to a multiplex circuit. The multiplex circuit is in turn coupled to leads 44, 46 which extend through the catheter 12 and into cable 47. Cable 47 is connectable to an image processing console 31 which houses image processing electronics as well as the monitor 30 in accordance with IVUS imaging technology well known in the art. When activated, the imaging transducer 38 emits ultrasound signals and receives back echos or reflections which are representative of the nature of the surrounding environment. The imaging transducer 38 provides an imaging signal from which an image of the surrounding structures can be created by signal processing apparatus located in an imaging console 31 and displayed on screen 30. A suitable IVUS phased array transducer as well as the accompanying circuitry and imaging console 31 may be obtained commercially from Volcano Corporation of Rancho Cordova, Calif. or Intravascular Research Limited (United Kingdom). As shown in FIGS. 1D, 1E, 2A and 2B and described in above-incorporated U.S. Pat. Nos. 6,746,464 (Makower), 6,726,677 (Flaherty et al.), 6,709,444 (Makower), 6,669,709 (Cohen et al.), 6,685,716 (Flaherty et al.), 6,685,648 (Flaherty et al.), 6,660,024 (Flaherty et al.), 6,579,311 (Makower), 6,561,998 (Roth et al.), 6,379,319 (Garibotto et al.), 6,375,615 (Flaherty et al.), 6,302,875 (Makower et al.), 6,283,983 (Makower et al.), 6,190,353 (Makower et al.), 6,159,225 (Makower), 6,068,638 (Makower) and 5,830,222 (Makower) and United States Patent Application Publication 2006/0241342 (Macaulay et al.), the orientation element 28 may comprise a marker that provides a predictive trajectory indication on a displayed image of the target. In this particular example, the orientation element 28 includes a marker structure 40 which includes imageable marker members 40a, 40b and 40c. This marker structure 40 is mounted on or in the catheter 12 in a known circumferential orientation relative to the side outlet port 16 or to the trajectory on which the penetrating guidewire 18 is expected to advance out of the side outlet opening 16. As seen in FIGS. 2A and 2B, the three imageable members 40a, 40b and 40c create corresponding images or artifacts (labeled as 40a-image, 40b-image and 40c-image) on the monitor 30 along with an image of the true blood vessel lumen or other target location T. One of these members 40a is specifically positioned to provide an image that is visually distinguisable from the others and which corresponds to the expected trajectory of the penetrating guidewire 18 so that the image (40a-image) created by that mamber 40a serves as the trajectory indicator. As seen in FIG. 2A, if the catheter 12 is in an incorrect rotational orientation, the trajectory indicator 40a-image does not extend into the target T but rather extends in a direction away from the target T. However, as seen in FIG. 2B, after the catheter 12 has been rotated to the correct rotational orientation, the trajectory indicator 40a-image extends directly toward or into the image of the target T.

It will be appreciated that, as an alternative to the use of a physical marker structure, the imaging transducer 38 could be mounted in a fixed position and a selected one (or selected ones) of the individual imaging elements (e.g., crystals) of the phased array may be selected as being in longitudinal alignment with the side outlet opening 16 or otherwise located so as to be indicative of the trajectory on which the penetrating guidewire 18 will subsequently advance from the catheter 12. The selected imaging element(s) will thus serve as penetrator-path-indicating imaging element(s) and will be electronically identified so as to form a visual penetrator path indicator (e.g., a line or pointer) on the monitor 30 of the imaging console 31.

Figure 3:
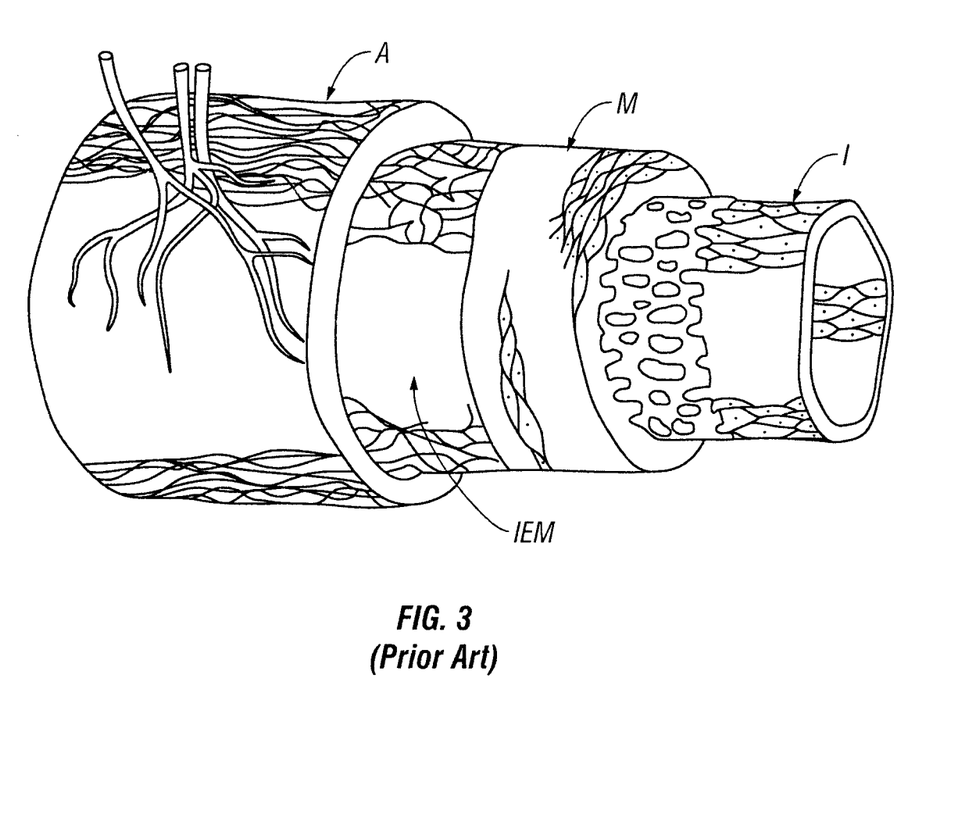
FIG. 3 is an anatomical diagram showing the histological layers of an artery.

FIG. 3 shows the anatomy of a typical artery wall and FIGS. 4A-4G show an example of a procedure in which the above-described catheter system 10 may be used to treat a CTO of an artery.

As shown in FIG. 3, the wall of an artery typically consists of three layers, the tunica intima ("intima"), tunica media M ("media") and the tunica adventitia A (adventitia). In some arteries an internal elastic membrane IEM is disposed between the media M and adventitia A.

Figure 4A:
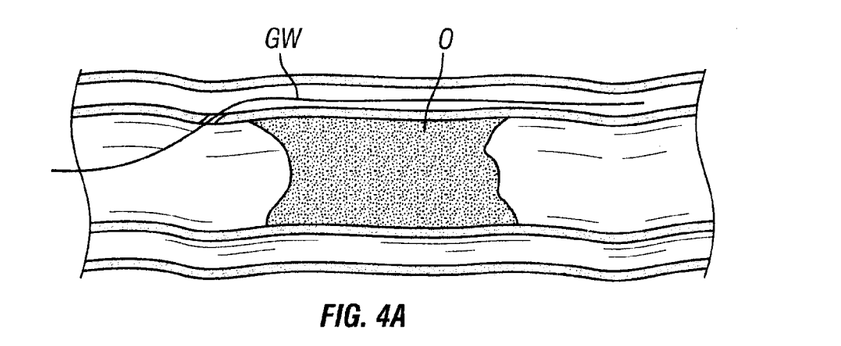
FIGS. 4A-4G show steps in a method for using the catheter device of FIG. 1 to perform a transluminal, catheter-based bypass of a CTO in an artery.

Initially, as shown in FIG. 4A and in accordance with techniques well known in the field of interventional cardiology and/or interventional radiology, the tracking guidewire GW is advanced into a subintimal space (i.e., beneath the intima I of the artery wall) adjacent to an obstruction O such that a distal portion of the tracking guidewire GW is distal to the obstruction O.

Figure 4B:
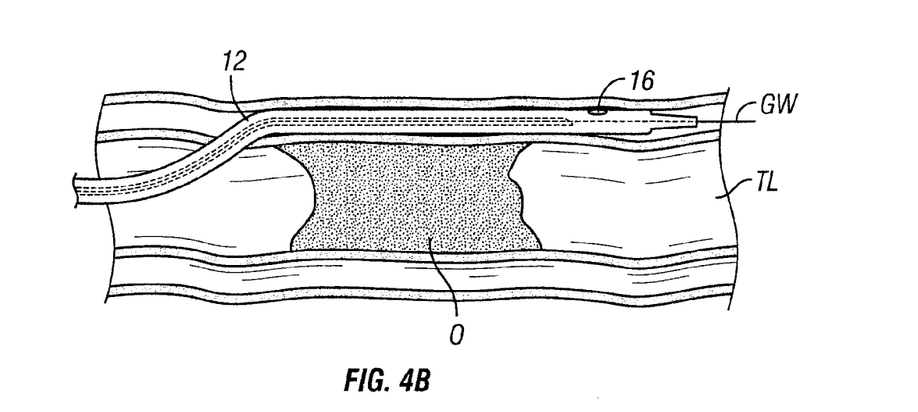

As seen in FIG. 4B, the catheter 12 is advanced over the tracking guidewire GW to a position where the side outlet opening 16 is distal to the obstruction O. However, in this example, the catheter 12 is initially positioned in an incorrect rotational orientation, such that the side outlet opening 16 is not directed toward the true lumen TL.

Figure 4C:
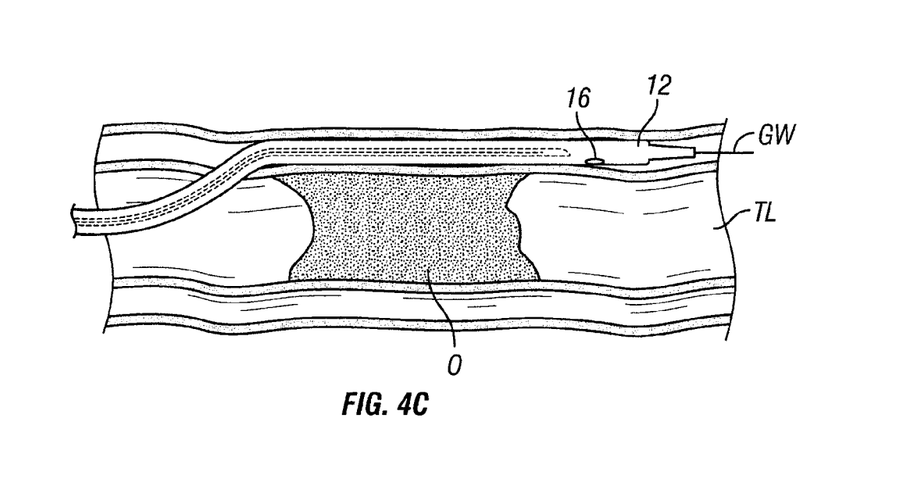

As shown in FIG. 4C, the optional orientation element 28 described above may be used by the operator to adjust the rotational orientation of the catheter 12 within the subintimal space to cause the side outlet opening 16 to be directed toward the true lumen TL and ensuring, or at least increasing the probability that, subsequent advancement of the penetrating guidewire 18 out of the side outlet opening 16 will cause the penetrating guidewire 18 to enter the true lumen TL of the artery, distal to the obstruction O.

Figure 4D:
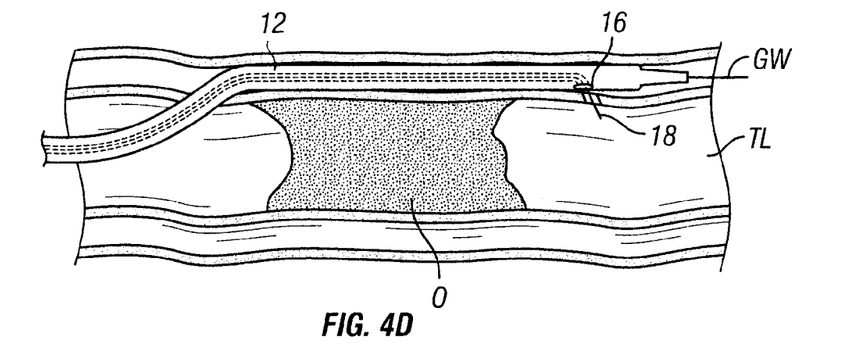
Figure 4E:
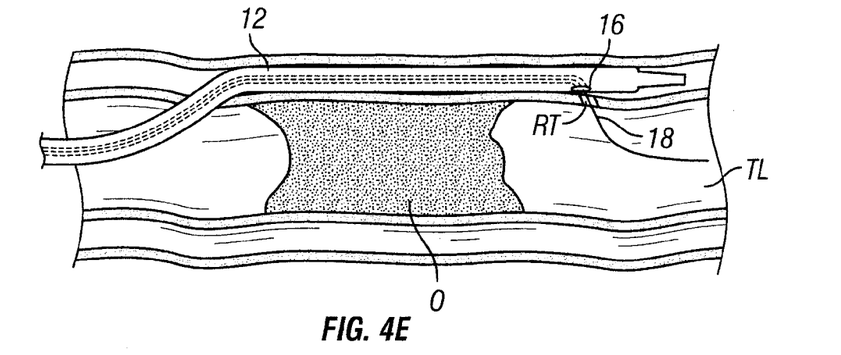

Thereafter, as shown in FIGS. 4D and 4E, the penetrating guidewire 18 is inserted into port 17 on proximal hub 14. The penetrating guidewire 18 is then advanced through lumen 36, through curved rigid tubular member 48 and out of side outlet opening 16, causing the penetrating guidewire 18 to form a reentry tract RT through adjacent tissue and to advance into the true lumen TL of the artery, distal to the obstruction O. The angle A at which the penetrating guidewire 18 advances may be sufficiently oblique to direct the penetrating guidewire 18 down the blood vessel lumen and to prevent the sharp distal tip 22 of the penetrating guidewire 18 from directly impinging against the opposite side of the blood vessel wall.

Figure 4F:
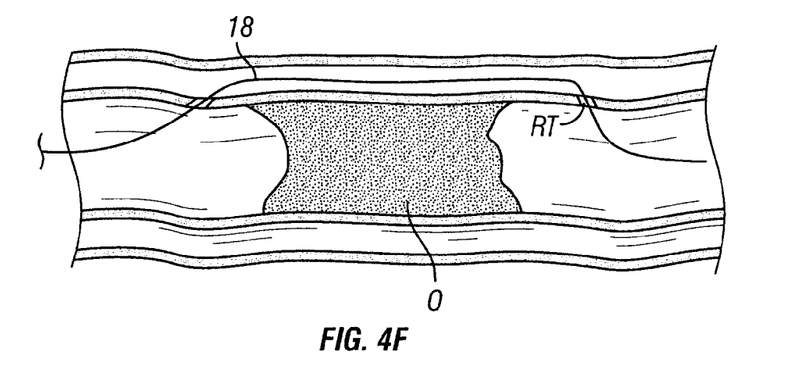

Thereafter, as shown in FIG. 4F, the catheter 12 and tracking guidewire GW are removed, leaving the penetrating guidewire 18 in place. Alternatively, prior to removing the catheter 12, the penetrating guidewire could be removed and replaced with an atraumatic guidewire, having already created an opening or tear between the subintimal and true lumen using the penetrating guidewire. Optionally, in some cases, it may be desirable to remove only the catheter 12, leaving the tracking guidewire GW in place as well.

Figure 4G:
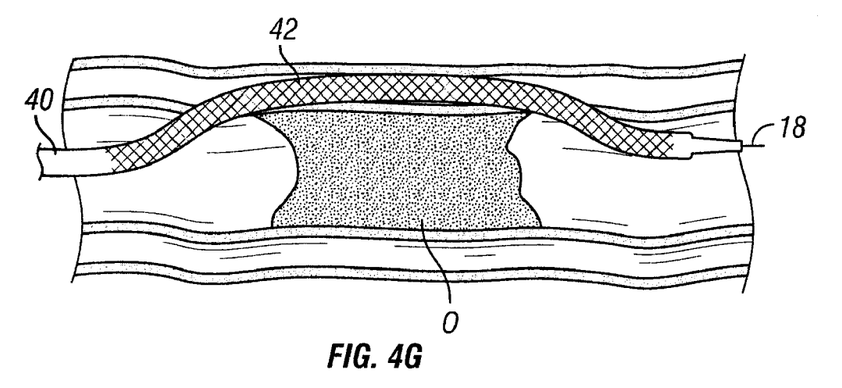
Figure 4H:
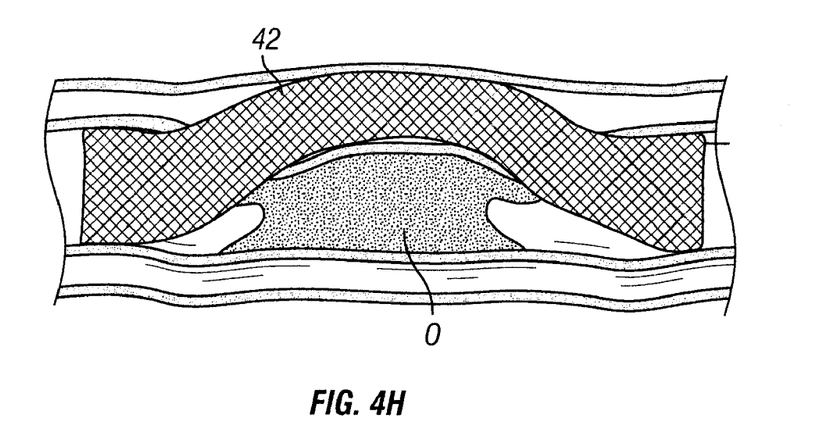

Thereafter, as seen in FIG. 4G, one or more working devices (e.g., balloon catheters, atherectomy catheters, stent delivery catheters, laser catheters, etc.) may then be advanced over the penetrating guidewire 18 and used to enlarge (e.g., dilate, debulk, bore, stent, etc.) the subintimal space and reentry tract RT. In this particular non-limiting example, the working device(s) comprises a balloon catheter 40 having a stent 42 mounted thereon. The balloon catheter 40 is advanced over the guidewire GW to a position where one end of the stent 42 is in the true lumen TL proximal to the obstruction O and the other end of the stent 42 is in the true lumen TL distal to the obstruction O. The balloon of the balloon catheter 40 is then inflated to dilate the subintimal space and to expand the stent 42. Thereafter, as seen in FIG. 4H, the balloon is deflated and the balloon catheter 40 is removed, leaving the stent 42 in an expanded configuration and creating a stented, subintimal bloodflow channel around the obstruction O as seen in FIG. 4H.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example not novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. A catheter system comprising:
    an elongate flexible catheter;
    a lumen that extends from a proximal insertion port to a side outlet opening;
    a penetrating guidewire that is separate and removable from the catheter, said guidewire being insertable into the proximal insertion port and thereafter advanceable through the lumen and out of the side outlet opening such that a distal portion of the guide wire is the only structure that extends out of the side outlet opening, said penetrating guidewire comprising a flexible guidewire body that is devoid of a lumen and which has a closed, sharp distal tip; and
    an orientation element useable to provide an indication of the trajectory on which the penetrating guidewire will advance from the catheter body;
    wherein the catheter has a longitudinal axis and wherein the lumen is configured such that the penetrating guidewire advances from the catheter at an angle that is less than 90 degrees relative to the longitudinal axis of the catheter.

2. A system according to claim 1 wherein a distal portion of the lumen comprises a curved, substantially rigid tubular member which deflects the penetrating guidewire out of the side outlet opening.

3. A system according to claim 2 wherein the curved, substantially rigid tubular member is formed of metal.

4. A system according to claim 1 wherein the orientation element comprises a) an imaging apparatus located on or in the catheter that is useable to obtain an image of a target location to which it is desired to advance the penetrating guidewire and b) a trajectory indicator that indicates a predicted trajectory on which the penetrating guidewire will advance relative to the image of the target location.

5. A system according to claim 4 wherein the imaging apparatus comprises an intravascular ultrasound imaging apparatus.

6. A system according to claim 4 wherein the trajectory indicator comprises an imageable member located on or in the catheter to create a visible trajectory indicator on an image received from the imaging apparatus.

7. A system according to claim 6 wherein the imageable member comprises a cage having a plurality strut members, a selected one or ones of said strut members providing said visible trajectory indicator.

8. A system according to claim 1 further comprising a tracking guidewire lumen extending through at least a portion of the catheter.

9. A system according to claim 1 wherein the penetrating guidewire exits the catheter at an angle of about 65 degrees relative to the longitudinal axis.

10. A system according to claim 1 wherein the catheter further comprises an atraumatic tip member at its distal end.

* * * * *